(12) United States Patent
Tedetti et al.

(10) Patent No.: US 9,274,055 B2
(45) Date of Patent: Mar. 1, 2016

(54) SUBMERSIBLE FLUOROMETER

(75) Inventors: Marc Tedetti, Marseilles (FR);
Madeleine Goutx, Marseilles (FR)

(73) Assignees: CENTRE NATIONAL DE LA RECHERCHE SCIENTIFIQUE (C.N.R.S.), Paris (FR), part interest;
UNIVERSITE D'AIX-MARSEILLE, Marseille (FR), part interest ( * ) Notice: Subject to any disclaimer, the term of this patent is extended or adjusted under 35 U.S.C. 154(b) by 0 days.

(21) Appl. No.: 14/002,186

(22) PCT Filed: Feb. 28, 2012

(86) PCT No.: PCT/EP2012/053337
§ 371 (c)(1),
(2), (4) Date: Aug. 29, 2013

(87) PCT Pub. No.: WO2012/119888
PCT Pub. Date: Sep. 13, 2012

(65) Prior Publication Data
US 2013/0327961 A1 Dec. 12, 2013

(30) Foreign Application Priority Data
Mar. 4, 2011 (FR) ...................................... 11 51780

(51) Int. Cl.
*G01N 21/64* (2006.01)
*G01N 21/85* (2006.01)
*G01N 33/18* (2006.01)

(52) U.S. Cl.
CPC .............. *G01N 21/64* (2013.01); *G01N 21/645* (2013.01); *G01N 21/6486* (2013.01);
(Continued)

(58) Field of Classification Search
CPC ................ G01N 21/64; G01N 21/645; G01N 2201/0218

USPC ....................................................... 250/461.1
See application file for complete search history.

(56) References Cited

U.S. PATENT DOCUMENTS 4,293,225 A * 10/1981 Wheaton et al. ............... 356/417
5,278,074 A * 1/1994 Rao et al. ......................... 436/52
(Continued)

FOREIGN PATENT DOCUMENTS

CN 201611335 U 10/2010
DE 3020168 A1 12/1981
(Continued)

OTHER PUBLICATIONS

Hudson et al., "Can Fluorescence Spectrometry Be Used as a Surrogate for the Biochemical Oxygen Demand (BOD) test in Water Quality Assessment? An Example from South West England", Science of the Total Environment, 2008, vol. 391, pp. 149-156, XP022398205.
(Continued)

*Primary Examiner* — Marcus Taningco
(74) *Attorney, Agent, or Firm* — Young & Thompson (57) ABSTRACT

A submersible fluorometer (10), includes:
an excitation module (40) for exciting the fluorophore; and
a detection module (42) for detecting the light emitted by the excited fluorophore,
wherein the excitation module (40) includes a first light source (44) including a first UV LED and having a first wavelength lower than 300 nm,
the excitation module (40) includes a second light source (46) including a second UV LED and having a second wavelength lower than 300 nm, the first and second wavelengths being different from each other,
and the fluorometer includes an electronic circuit having a plurality of printed circuits positioned one below the other.

19 Claims, 5 Drawing Sheets

(52) U.S. Cl.
CPC ......... *G01N 21/8507* (2013.01); *G01N 33/182* (2013.01); *G01N 33/1886* (2013.01); *G01N 2201/0218* (2013.01); *G01N 2201/062* (2013.01); *G01N 2201/127* (2013.01)

(56) References Cited

U.S. PATENT DOCUMENTS

| 6,563,585 | B1 * | 5/2003 | Rao et al. ..................... 356/436 |
| 7,470,917 | B1 * | 12/2008 | Hoang et al. ................. 250/458.1 |
| 8,017,928 | B2 * | 9/2011 | McStay et al. ............. 250/559.4 |
| 2010/0068821 | A1 * | 3/2010 | St. Germain ................. 436/140 |

FOREIGN PATENT DOCUMENTS

| EP | 0459846 | A2 | 12/1991 |
| GB | 2024419 | A | 1/1980 |
| GB | 2078941 | A | 1/1982 |
| WO | 03023379 | A1 | 3/2003 |
| WO | 2010063856 | A1 | 6/2010 |

OTHER PUBLICATIONS

International Search Report, dated Jun. 7, 2012, from corresponding PCT application.

* cited by examiner

SUBMERSIBLE FLUOROMETER

The present invention relates to a submersible fluorometer intended to be mounted on an underwater system for studying fluorescent aromatic compounds of the aquatic environment, each aromatic compound having at least one fluorophore, of the type comprising:
- an excitation module suitable for exciting the fluorophore; and
- a detection module suitable for detecting the light emitted by the excited fluorophore.

Fluorescence is a spectroscopic method that has been widely used for approximately 20 years to study the distribution, composition and dynamics of the dissolved organic matter (DOM) in the aquatic environment.

At this time, spectrophotometric laboratory analyses make it possible to obtain a detailed mapping over a large spectral domain of the fluorescent DOM (DOM-F) composition of a discrete sample of natural water. These analyses show that the DOM-F is made up of various fluorophores of the "polluting" type, with polycyclic aromatic hydrocarbons (PAHs) such as phenanthrene (Phe), of the "protein" type, such as tryptophan (Try), as well as of the "humic substance" type, such as soil humic acids (SHA) and marine humic acids (MHA).

Laboratory analyses on discrete samples are necessary, but nevertheless remain insufficient to assess the variability at a high spatial and temporal frequency of the biogeochemical parameters in the aquatic medium. The laboratory fluorometers used, which are very bulky, generally use high-energy xenon lamps as their UV light source.

That is why, for approximately 10 years, the use of optical sensors onboard underwater platforms or vehicles has been experiencing rapid growth. This platform/sensor coupling makes it possible to increase the spatiotemporal frequency of biogeochemical measurements considerably.

Submersible optical sensors are essentially fluorometers, photometers or diffusion meters which, through the fluorescence, absorbance or diffusion properties of the material, measure biogeochemical variables.

The underwater platforms or vehicles, which may be autonomous or wired, include gliders, profiling floats, stationary or drifting buoys, propeller vehicles (AUVs) and remotely operated vehicles (ROVs), some being able to spend from several weeks or months (gliders) to several years (profiling floats) at sea.

However, the submersible optical sensors commercially available today are not suitable for being mounted on all existing types of underwater vehicles.

The invention aims to propose a submersible fluorometer that makes it possible to study the main fluorescent aromatic compounds present in the aquatic medium and that may be mounted on all existing types of underwater vehicles.

To that end, the invention relates to a fluorometer of the aforementioned type, characterized in that the excitation module comprises a first light source having a first UV LED and having a first wavelength smaller than 300 nm.

The fluorometer according to the invention may include one or more of the following features:
- the first wavelength may be substantially equal to 250 nm,
- the detection module may include a first photodiode, a first collimator lens, and a first optical interference filter,
- the first optical interference filter may be centered substantially over 360 nm or 427 nm,
- the fluorometer may comprise a fastening part suitable for being fastened on the underwater system and a measuring part suitable for being submerged,
- the measuring part may include a protective cover protecting against the ambient light,
- the fluorometer may have a substantially cylindrical shape,
- the excitation module may include a second light source having a second UV LED and having a second wavelength smaller than 300 nm, the first and second wavelengths being different from each other,
- the second wavelength may be substantially equal to 280 nm,
- the detection module may include a second photodiode, a second collimator lens, and a second optical interference filter,
- the second optical interference filter may be centered substantially over 340 nm or over 405 nm,
- the fluorometer may be suitable for studying polycyclic aromatic hydrocarbons such as phenanthrene, amino acids such as tryptophan, and organic matter source tracers such as soil humic acids and marine humic acids,
- the fluorometer may be suitable for descending to depths of up to 1000 m,
- the fluorometer may be suitable for being mounted on any type of underwater system, whether autonomous or wired, such as gliders, profiling floats, stationary or drifting buoys, propeller vehicles (AUVs) and remotely operated vehicles (ROVs),
- the fluorometer includes an electrical circuit including a plurality of printed circuits positioned below one another,
- the electronic circuit includes 3 four-layer printed circuits, an excitation circuit controlling the excitation module, a detection circuit controlling the detection module, and a monitoring circuit,
- the detection circuit is provided with an analog-digital converter,
- the monitoring circuit uses the digital data from the analog-digital converter to synchronize the excitation module and the detection module,
- the fluorometer has a substantially cylindrical shape around an axis of revolution, the three circuits being positioned below one another so as to be substantially parallel to each other and concentric around the axis of revolution.

Figure 1:
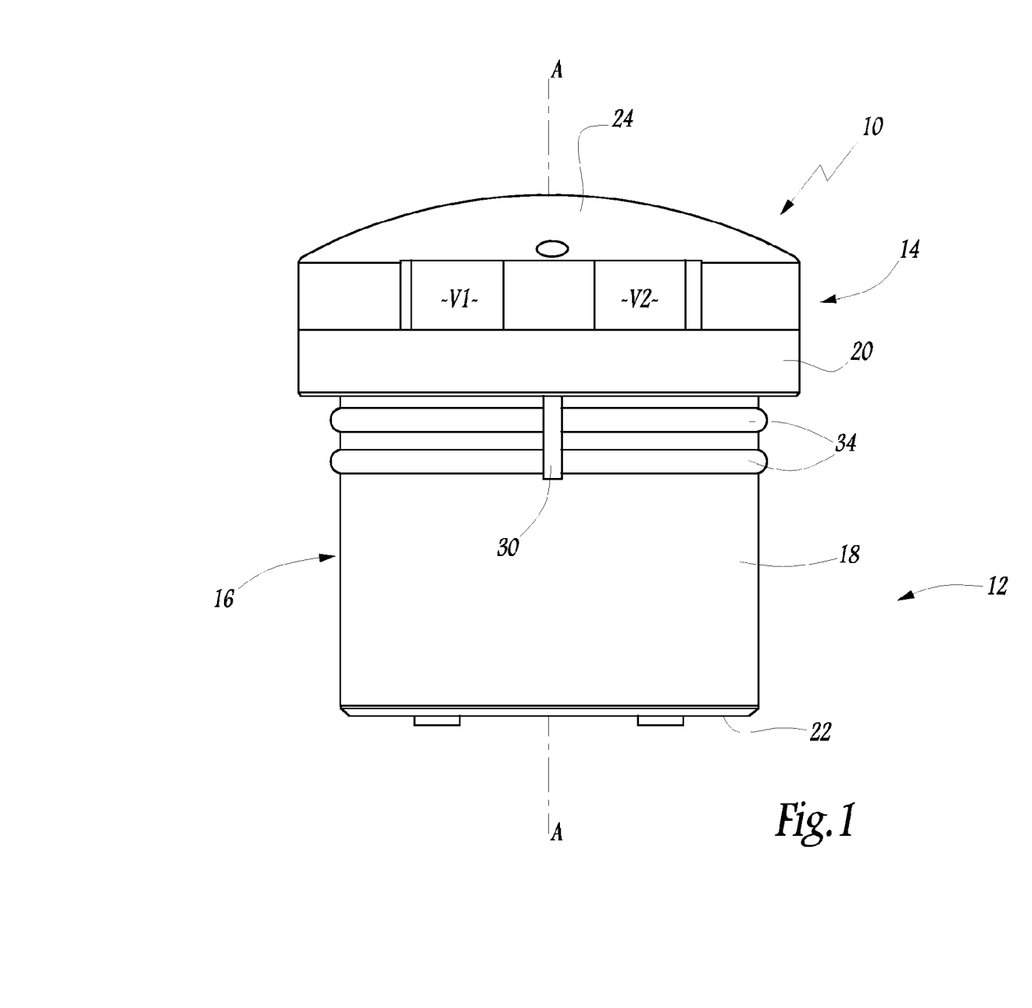
FIG. 1 is a side view of a fluorometer according to the invention.

The invention will be better understood upon reading the following description, provided solely as an example and done in reference to the appended drawings, in which:

FIG. 1 illustrates a fluorometer 10 suitable for being mounted on an underwater system (not shown) for the simultaneous study of two fluorescent aromatic compounds in the aquatic environment.

The fluorometer 10 comprises a fastening part 12 suitable for being fastened on the underwater system and a measuring part 14 suitable for being submerged in the water so as to be in contact with the measurement medium, such as fresh water or seawater.

The fastening part 12 comprises a housing 16 including a substantially cylindrical body 18 with axis A-A extended at one end by a substantially annular flange 20.

The flange 20 has an outer diameter larger than that of the body 18.

Figure 2:
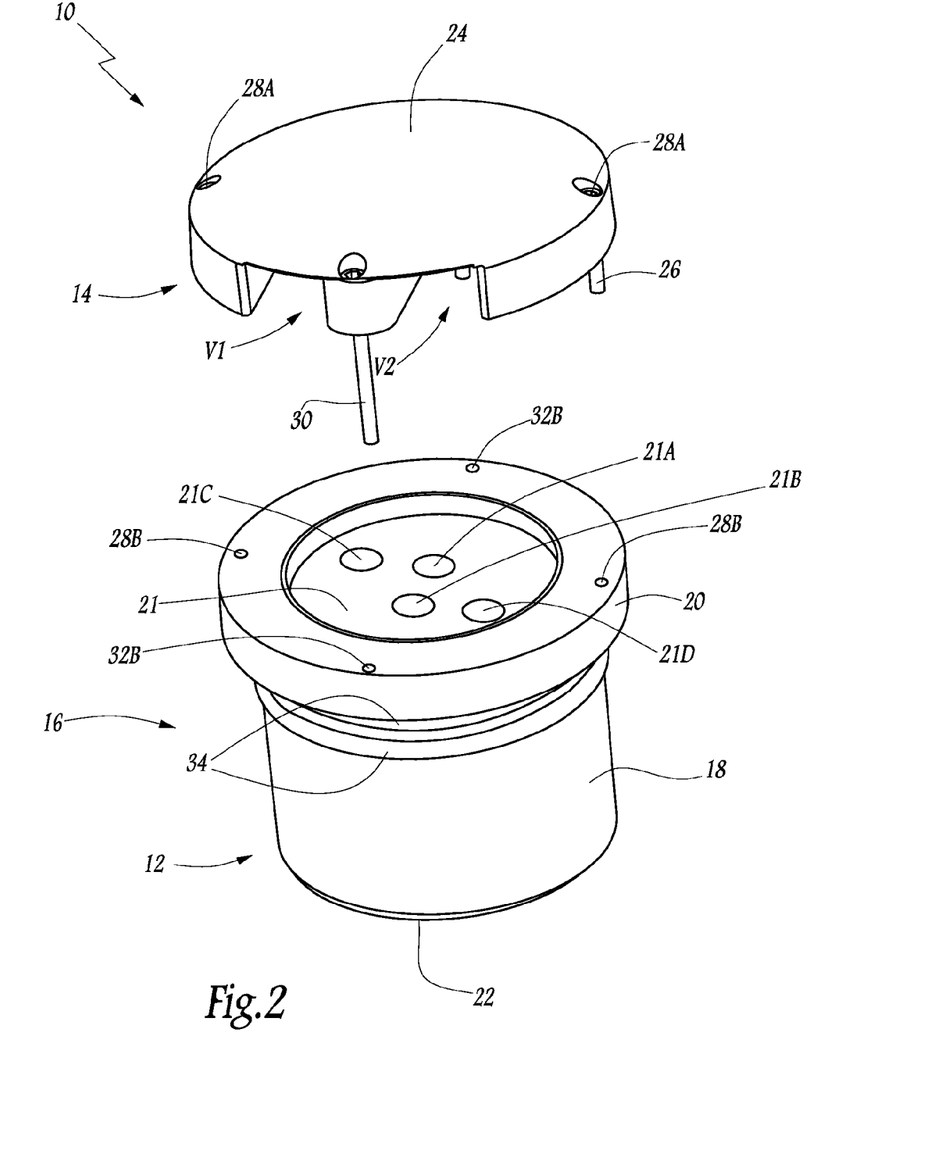
FIG. 2 is an exploded perspective top view of the fluorometer of FIG. 1.
Figure 3:
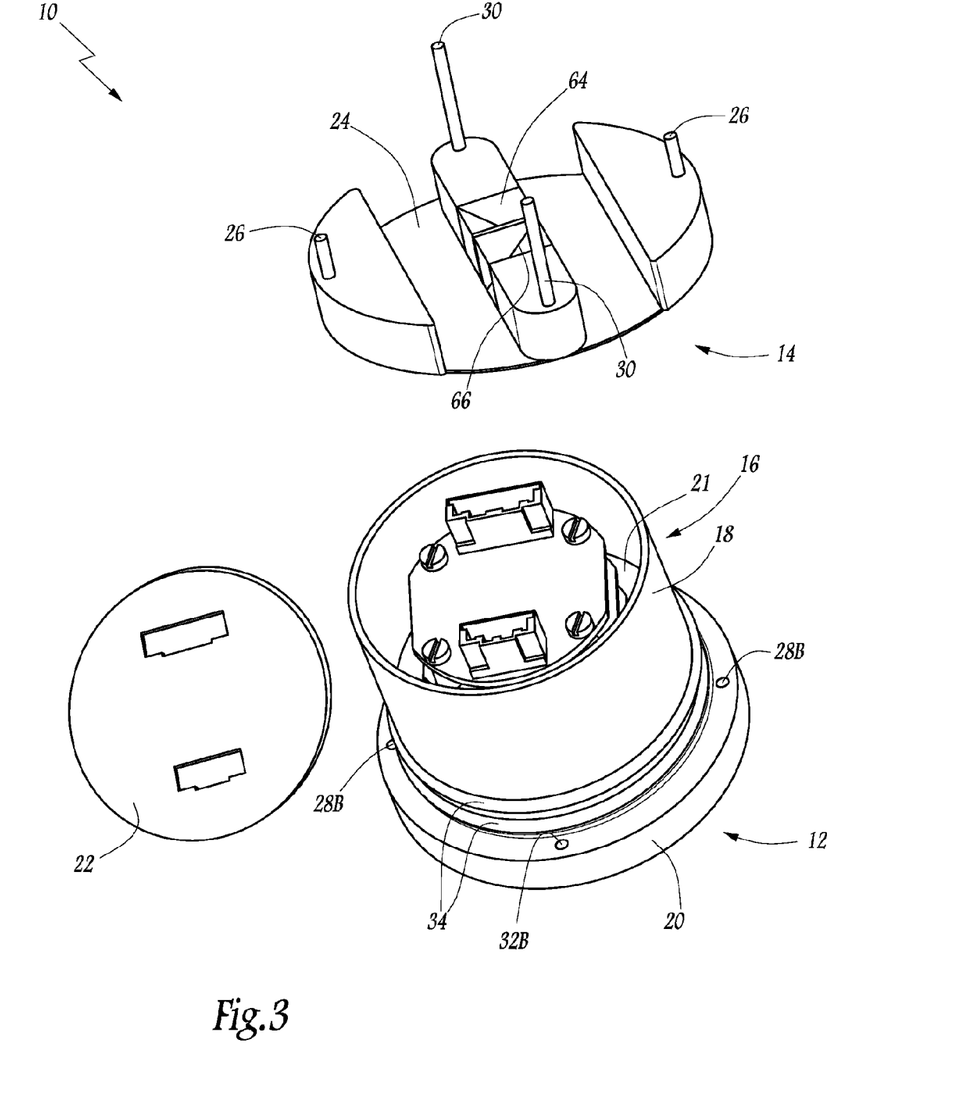
FIG. 3 is an exploded perspective bottom view of the fluorometer of FIG. 1.

In reference to FIGS. 2 and 3, the body 18 and the flange 20 delimit respective inner chambers separated from each other by a separating wall 21.

The separating wall 21 includes four through openings 21A, 21B, 21C and 21D intended for the passage of light between the inside and the outside of the fluorometer 10, as will be explained in more detail hereafter.

The housing 16 is made from aluminum, the flange 20 being integral with the body 18. The separating wall 21 is made up of an attached part, fastened, for example by gluing, to the flange 20.

The fastening part 12 comprises a plate 22 for covering the end of the body 18 opposite the flange 20.

The covering plate 22 is in the shape of a disk with a diameter substantially equal to the diameter of the body 18.

The covering plate 22 is made from aluminum and fastened to the body 18, for example by gluing.

The measuring part 14 comprises a substantially dome-shaped cover 24.

The cover 24 includes a central portion designed to receive optical components and delimits two optical measuring paths V1 and V2, in each of which water can flow, as will be seen later.

The cover 24 is made from polyurethane resin so as to protect the measuring part 14 from the natural ambient light.

The cover 24 is fastened to the housing 16 by two assembly screws 26 passing through two diametrically opposite assembly orifices 28A, formed on the circumference of the cover 24, and two diametrically opposite assembly orifices 28B formed on the circumference of the flange 20, the assembly orifices 28A, 28B being positioned matching in pairs.

The fluorometer 10 is fastened in the dry compartment of the underwater system by two fastening screws 30 passing through two diametrically opposite fastening orifices 32A formed on the circumference of the cover 24 and two diametrically opposite fastening orifices 32B formed on the circumference of the flange 20, the fastening orifices 32A, 32B being positioned matching in pairs.

The fastening orifices 32A, 32B are angularly offset relative to the respective assembly orifices 28A, 28B by an angle substantially equal to 90°.

O-rings 34, for example two O-rings, are provided on the body 18 of the housing 16 to guarantee sealing of the fluorometer 10 with the underwater system.

As previously mentioned, the fluorometer 10 is suitable for simultaneously detecting/quantifying two fluorescent aromatic compounds of interest, one aromatic compound being associated with an optical measuring path and each aromatic compound having its own fluorophore.

Figure 4:
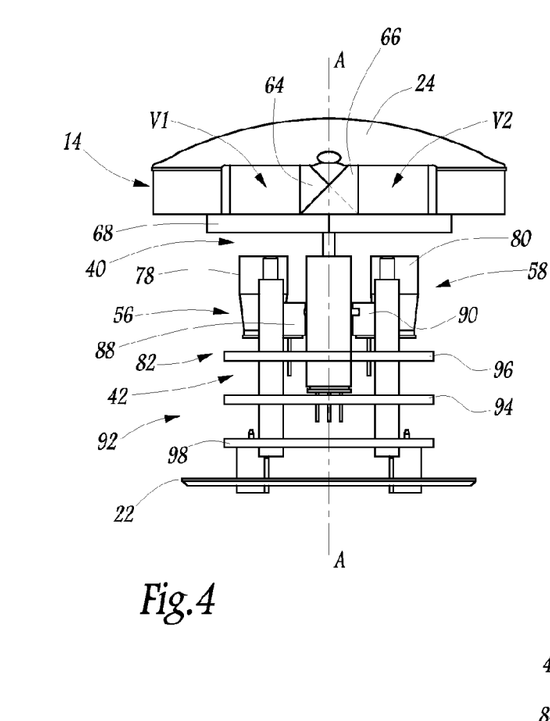
FIG. 4 is a cross-sectional view of part of the fluorometer of FIG. 1.
Figures 5, 6:
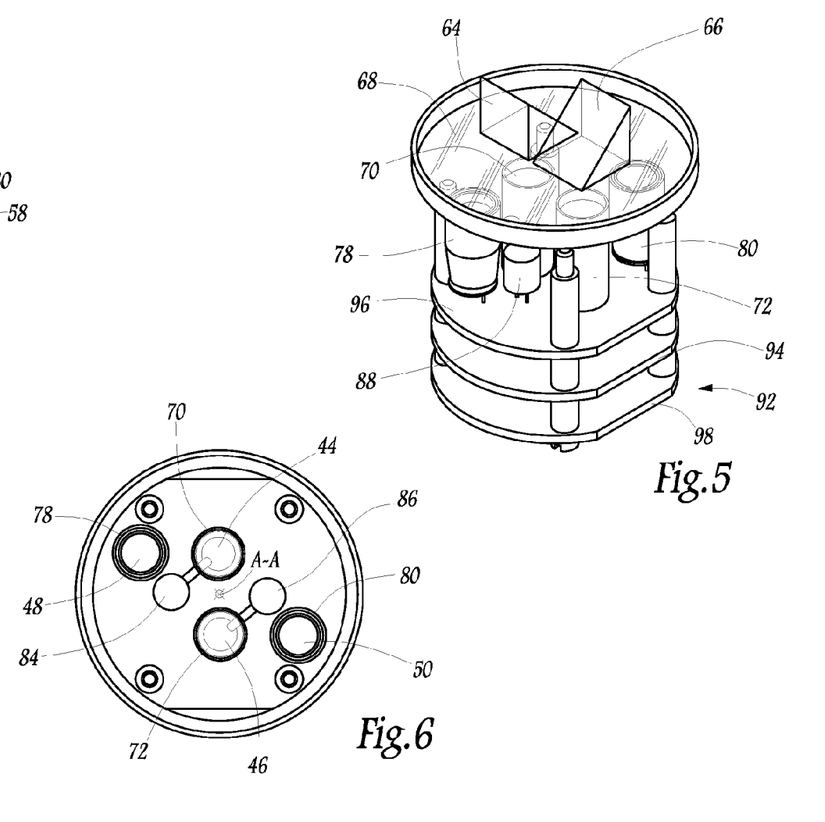
FIG. 5 is a perspective view of part of the fluorometer of FIG. 1.
FIG. 6 is a top view of part of the fluorometer of FIG. 1.

Thus, and as shown in FIGS. 4 to 6, the fluorometer 10 comprises an excitation module 40 suitable for exciting the fluorophores and a detection module 42 suitable for detecting light emitted by the excited fluorophores.

In fact, when a photon is absorbed by a fluorophore, i.e., a fluorescent compound, the latter goes from its fundamental electronic state to an excited electronic state. The return to the fundamental state is done by the very rapid emission of a lower-energy photon, therefore with a greater wavelength, than that of the excitation photon, since there is an energy loss due to vibrational relaxation. The light emitted by the fluorophore is the fluorescence light (or emission light). Consequently, a fluorophore is characterized by a specific pair of wavelengths: an excitation wavelength $\lambda Ex$ and an emission wavelength $\lambda Em$, $\lambda Em$ always being greater than $\lambda Ex$. Furthermore, the intensity of the fluorescence light of the fluorophore is proportional to its concentration in the considered medium. Most of the fluorophores are aromatic compounds that have a cyclical molecular structure.

In this way, the excitation module 40 comprises a first light source 44 for the optical measuring path V1 and a second light source 46 for the optical measuring path V2.

The first and second light sources 44, 46 are selective light sources of the UV LED type, which make it possible to excite the fluorophores of interest present in the studied medium at a specific wavelength.

The detection module 42 comprises, for each measuring path V1 and V2, a photon detector 48, 50, an interferential optical filter (only the filter 54 of the measuring path V2 is visible in FIG. 7), and an optical system 56, 58.

The photon detectors 48, 50 are non-selective wavelength photon detectors that make it possible to measure the intensity of the fluorescence light of the fluorophores in return.

In the example illustrated here, the photon detectors 48, 50 are silicon photodiodes.

The optical fibers 54 make it possible to select the emission wavelength $\lambda Em$ that are detected by the photodiodes 48, 50.

The optical systems 56, 58 make it possible to reorient the excitation and fluorescence light flows in the desired directions.

To that end, each optical system 56, 58 comprises a biconvex quartz lens (only the lens 62 of the measuring path V2 is visible in FIG. 7), and a quartz prism 64, 66 inclined at 45°.

The optical systems 56, 58 comprise a common quartz porthole 68. The optical components specific to the targeted fluorophore are the LED and the interferential filter.

The optical measuring path V1 of the fluorometer 10 is dedicated to the detection/quantification of phenanthrene (Phe), which is a polyaromatic hydrocarbon (PAH) with three fused benzene rings ($C_{14}H_{10}$). Phe is one of the most abundant PAHs in the aquatic environment and it is additionally one of the most fluorescent PAHs with a maximum fluorescence at $\lambda Ex/\lambda Em$: 235-255/345-370 nm. Phe is a good indicator of petroleum contaminations in an aquatic medium.

It is therefore detected using a UV LED 44 emitting at 250 nm and an interferential filter centered at 360 nm ($\lambda Ex1/\lambda Em1$: 250/360 nm). The bandwidths (FWHM for Full Width Half Maximum) of the LED 44 and the filter are 12 nm.

Alternatively, by replacing the interferential filter centered at 360 nm with an interferential filter centered at 427 nm, the measuring path V1 ($\lambda Ex1/\lambda Em3$: 250/427 nm) becomes operative for the detection/modification of soil humic acids (SHA).

The SHAs, which have a maximum fluorescence at $\lambda Ex/\lambda Em$: 230-260/400-440 nm, are good organic matter source tracers.

The optical measuring path V2 of the fluorometer 10 is dedicated to the detection/quantification of tryptophan (Try), which is an aromatic amino acid ($C_{11}H_{12}N_2O_2$). Try, one of the fluorescence maximums of which is at $\lambda Ex/\lambda Em$: 265-285/335-360 nm, is a good indicator of the presence of fecal bacteria and wastewater contamination.

It is therefore detected using a UV LED 46 emitting at 280 nm and an interferential filter 54 centered at 340 nm ($\lambda Ex2/\lambda Em2$: 280/340 nm). The FWHMs of the LED 46 and the filter 54 are 12 nm.

Alternatively, by replacing the interferential filter 54 centered at 340 nm with an interferential filter centered at 405 nm, the measuring path V2 (λEx2/λEm4: 280/405 nm) becomes operative for the detection/modification of marine humic acids (MHA).

MHAs, which have a maximum fluorescence at λEx/λEm: 280-310/380-420 nm, are good organic matter source tracers.

The fluorometer 10 therefore allows the simultaneous detection/collimation of two aromatic compounds of interest in the aquatic medium, a single compound being detected optically, and for each path, the choice being able to be made between two compounds based on the interferential filter used.

The optical path V1 (LED 250 nm, filter 360 or 427 nm) is dedicated to measuring Phe or SHAs, while the optical path V2 (LED 280 nm, filter 340 or 405 nm) is dedicated to measuring Try or MHAs.

There are therefore four possible combinations of V1/V2: Phe/Try, SHA/Try, Phe/MHA and SHA/MHA.

The choice of the configuration is made by the user when ordering the fluorometer. The configuration may be changed at any time by the manufacturer upon request by the user, for example based on the type of oceanographic mission to be carried out.

Figure 7:
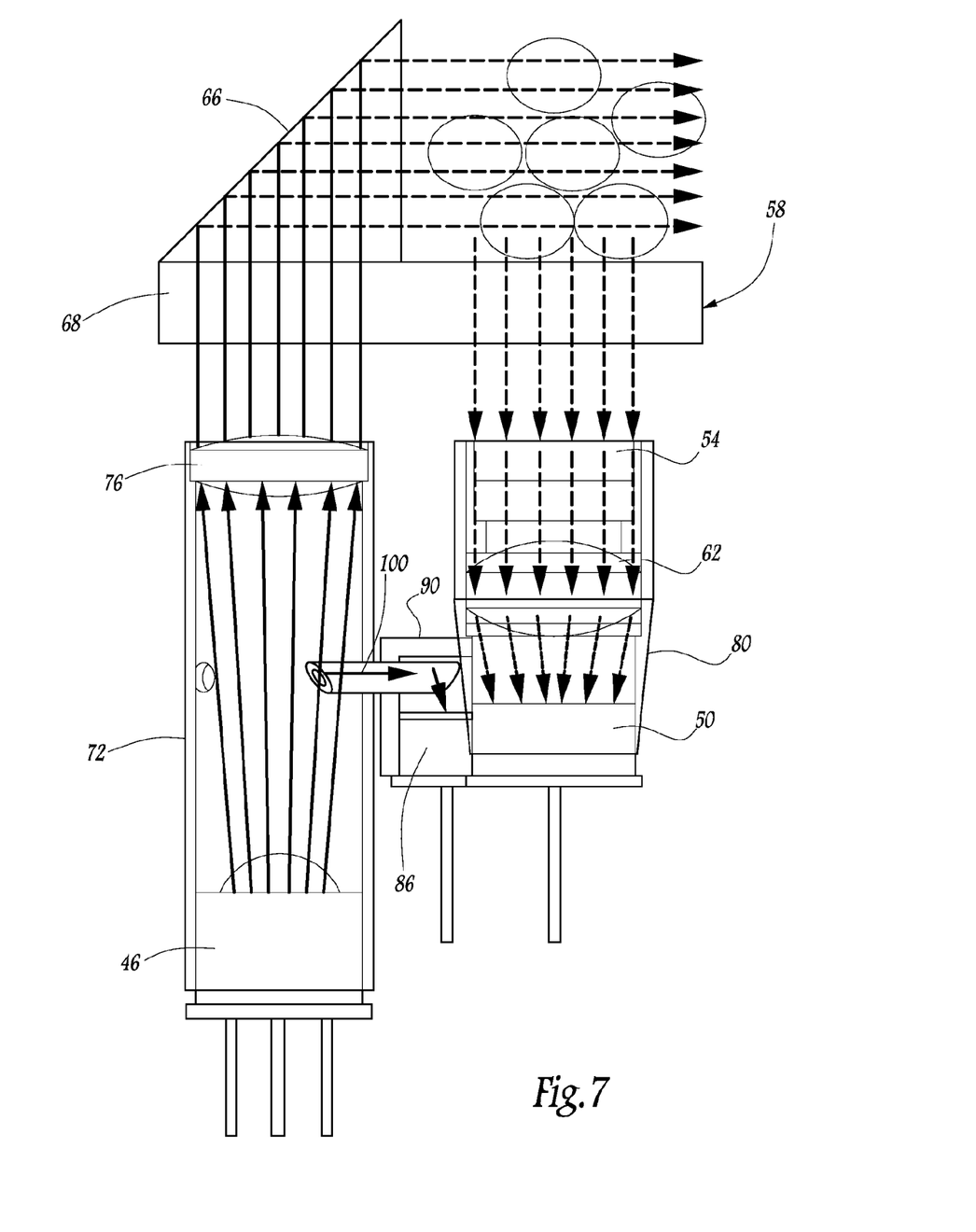
FIG. 7 is a diagram illustrating the operating principle of the fluorometer of FIG. 1.

The UV LEDs 44, 46 are each positioned in an excitation bush 70, 72 and associated with a quartz biconvex lens, only the lens 76 of the measuring path V2 being visible in FIG. 7.

The excitation bushes 70, 72 are positioned vertically upward, diametrically opposite each other, adjacent to the axis A-A and across from the through openings 21A, 21B of the separating wall 21.

The photodiodes 48, 50 are each positioned in a detection bush 78, 80 and associated with the interferential filter and the lens 54 and 62, respectively, regarding the measuring path V2.

The detection bushes 78, 80 are positioned vertically upward, diametrically opposite each other, adjacent to the corresponding excitation bushes 70, 72 and across from through openings 21C, 21D of the separating wall 21.

The prisms 64, 66 are embedded in the central portion of the cover 24 so as to be symmetrical relative to the axis A-A.

The quartz porthole 68 is received in the inner chamber formed by the flange 20 of the housing 16 and for example fixed by gluing.

The fluorometer 10 further comprises a monitoring module 82 including, for each measuring path P1, P2, a reference detector 84, 86 that measures the intensity of the radiation emitted by the respective LED 44, 46 so as to correct the fluorescence signal for any fluctuations of the LED 44, 46.

In the example illustrated here, the reference detectors 84, 86 are silicon photodiodes that are each positioned in a monitoring bush 88, 90.

The monitoring bushes 88, 90 are positioned vertically upward, diametrically opposite each other and adjacent to the corresponding excitation bushes 70, 72 and the corresponding detection bushes 78, 80.

The fluorometer 10 comprises an electronic system 94 powering the two measuring paths V1 and V2. The electronic system 92 is thus shared by the two optical paths.

The electronic system 92 includes 3 four-layer printed circuits: an excitation circuit 94 dedicated to controlling the LEDs 44, 46, a detection circuit 96 used to control the silicon photodiodes 48, 50, 84, 86, and a monitoring circuit 98.

Alternatively, the detection circuit 96 is also used to convert the signals recorded by the silicon photodiodes 48, 50, 84 and 86. This conversion is a conversion of the analog-digital type. Thus, the detection circuit 96 comprises an analog-digital converter capable of performing conversions of the analog-digital type.

The monitoring circuit 98 is, according to the example of FIGS. 4 and 5, capable of receiving the digital data from the detection circuit 96.

Furthermore, the monitoring circuit 98 makes it possible to monitor the synchronization of the LEDs 44 and 46 and the photodiodes 48, 50, 84, 86.

Alternatively, the monitoring circuit 98 serves as an I2C interface between the fluorometer 10 and the underwater vehicle that receives it. An I2C interface is easy to use.

The electronic system 92 procures many advantages. It makes it possible to obtain very dynamic adjustable measurements.

Thus, as an example, the user can thus vary the integration duration of the measurement considerably. The integration duration of the measurement corresponds to the time interval during which an LED 44, 46 is lit and during which the fluorescence light signal is measured by the associated photodiode 48, 50, 84, 86. In the described embodiment, the integration duration varies from 2 ms (milliseconds) to 2000 ms.

As an additional illustration of the very dynamic measurements procured by the electronic system 92, the electrical capacity of the capacitor of the analog-digital converter of the detection circuit 96 may also vary considerably, in particular on request by the user. As an example, this electrical capacity may be equal to multiple values. In the described embodiment, the capacity is equal to the following values: 3 pF (picofarads), 12 pF, 25 pF, 36 pF, 50 pF, 60 pF, 73 pF or 87.5 pF.

Having very dynamic adjustable measurements has the advantage of allowing good tunability of the sensitivity of the fluorometer 10. Furthermore, this makes it possible to consider adapting the measurement strategy based on the studied environment. The measurement strategy used may also account for the underwater vehicle on which the fluorometer 10 is integrated.

The three circuits 94, 96, 98 are positioned below one another so as to be substantially parallel to each other and concentric to the axis A-A.

In the considered example, the three circuits 94, 96, 98 are oriented upward, or toward the measuring paths V1 and V2.

The electronic system 92 thus makes it possible to reduce the bulk of the fluorometer 10 considerably. It in particular avoids wires or connector technology becoming scattered inside the fluorometer 10.

This also results in a decrease in parasitic electromagnetic noise.

Furthermore, access to the optical components of the fluorometer is made easier.

In fact, all of the optical components, except the prisms 64, 66, as well as the electronic circuits are positioned inside the housing 16.

Furthermore, all of the optical components of the fluorometer 10 are of UV grade quality to be completely transparent to the short wavelength UV radiation emitted by the LEDs.

The fluorometer 10 is an autonomous sensor electrically behaving like a "slave" I2C module relative to a "master" I2C controller, in this case the central computer of the underwater system.

In terms of communication, in the case of a fluorometer suitable for Phe/Try detection, the fluorometer 10 comprises four measuring paths that operate simultaneously: one path for assaying Phe, one path for assaying Try, one path for monitoring the LED 44 (associated with the Phe), and one for monitoring the LED 46 (associated with the Try).

Thus formed, the fluorometer 10 has smaller dimensions of approximately 75.6 mm in diameter and 75 mm in length.

Additionally, the weight of the fluorometer 10 is also reduced, approximately 300 g.

The materials (aluminum, polyurethane) and the mechanical architecture used guarantee the fluorometer 10 a compression strength of up to 100 bars, or 1000 m deep.

The fluorometer 10 is supplied with 10-12 V by the cells or batteries of the underwater system and consumes approximately 50 mA to 12 V, or approximately 0.6 W.

The operation of the fluorometer 10 is explained below in reference to FIG. 7 and for the measuring path V2 for Try.

The flow of photons emitted by the UV LED 46 is collimated/focused by the lens 76, passes through the quartz porthole 68, and lastly arrives on the quartz prism 66 that is positioned in the extension of the excitation bush 72.

The prism 66 orients the flow of photons toward the outside of the fluorometer 10, i.e., in the surrounding medium (fresh or sea water), to excite the target molecules that are present there.

The two prisms 64, 66 being positioned symmetrically relative to the axis A-A, the radiation coming from the two LEDs 44, 46 is sent back in opposite directions, and there is therefore no risk of one optical path disrupting the other.

The excited molecules in return emit a fluorescent light, a fraction of which crosses through the porthole 68 and penetrates the detection bush 80.

The interferential filter 54 allows the wavelength of interest λEm to pass while absorbing all of the other wavelengths.

The flow of photons of interest that passes through the filter 54 is then collimated/focused by the lens 62 to be optimally collected by the photodiode 50, which converts the received light signal into an electrical signal.

The monitoring bush 90 is used to monitor the flow of photons emitted by the LED 46. An optical fiber piece 100 makes it possible to transfer a certain quantity of photons emitted by the LED 46 toward the reference photodiode 86. Thus, if the flow of photons emitted by the LED 46 varies over time, the fluorescence measurement may be corrected owing to the control measurement, the fluorescence intensity being directly proportional to the intensity of the excitation light.

The invention therefore proposes a submersible fluorometer with two measuring paths with short wavelength (less than 300 nm) UV light sources for the detection/modification of targeted aromatic compounds in the aquatic environment.

The fluorometer according to the invention is designed, from a mechanical (very reduced size and weight) and electrical (very low consumption) perspective, to be integrated very easily into any type of autonomous or wired underwater platforms/vehicles: gliders, profiling floats, propeller vehicles (AUVs), buoys, remotely operated vehicles (ROVs), etc.

Of course, the fluorometer according to the invention may be suitable for analyzing a single aromatic compound or several aromatic compounds, depending on the space available to receive the fluorometer on the underwater system.

The invention claimed is:

1. A submersible fluorometer intended to be mounted on an underwater system for studying fluorescent aromatic compounds of the aquatic environment, each aromatic compound having at least one fluorophore, of the type comprising:
    an excitation module suitable for exciting the fluorophore; and
    a detection module suitable for detecting the light emitted by the excited fluorophore,
    wherein the excitation module comprises a first light source having a first UV LED and having a first wavelength smaller than 300 nm,
    and the excitation module includes a second light source having a second UV LED and having a second wavelength smaller than 300 nm, the first and second wavelengths being different from each other,
    and the fluorometer includes an electrical circuit including a plurality of printed circuits positioned below one another,
    wherein the electrical circuit includes three four-layer printed circuits, an excitation circuit controlling the excitation module, a detection circuit controlling the detection module, and a monitoring circuit, the three four-layer printed circuits being one below another in vertical registration with each other.

2. The fluorometer according to claim 1, wherein the detection circuit is provided with an analog-digital converter.

3. The fluorometer according to claim 2, wherein the monitoring circuit uses the digital data from the analog-digital converter to synchronize the excitation module and the detection module.

4. The fluorometer according to claim 1, wherein the fluorometer has a substantially cylindrical shape around an axis of revolution, the three circuits being positioned below one another so as to be substantially parallel to each other and concentric around the axis of revolution.

5. The fluorometer according to claim 1, wherein the fluorometer comprises a fastening part suitable for being fastened on the underwater system and a measuring part suitable for being submerged.

6. The fluorometer according to claim 5, wherein the measuring part includes a protective cover protecting against the ambient light.

7. The fluorometer according to claim 1, wherein the first wavelength is substantially equal to 250 nm and the second wavelength is substantially equal to 280 nm.

8. The fluorometer according to claim 1, wherein the detection module includes:
    a first photodiode, a first collimator lens, and a first optical interference filter,
    a second photodiode, a second collimator lens, and a second optical interference filter.

9. The fluorometer according to claim 8, wherein the first optical interference filter is centered substantially over 360 nm or 427 nm.

10. The fluorometer according to claim 9, wherein the second optical interference filter is centered substantially over 340 nm or over 405 nm.

11. The fluorometer according to claim 1, wherein the fluorometer is suitable for studying polycyclic aromatic hydrocarbons such as phenanthrene (Phe), amino acids such as tryptophan (Try), and organic matter source tracers such as soil humic acids (SHA) and marine humic acids (MHA).

12. The fluorometer according to claim 1, wherein the fluorometer is suitable for descending to depths of up to 1000 m.

13. The fluorometer according to claim 1, wherein the fluorometer is suitable for being mounted on any type of underwater system, whether autonomous or wired, such as gliders, profiling floats, stationary or drifting buoys, propeller vehicles and remotely operated vehicles.

14. The fluorometer according to claim 2, wherein the fluorometer is suitable for being mounted on any type of underwater system, whether autonomous or wired, such as gliders, profiling floats, stationary or drifting buoys, propeller vehicles and remotely operated vehicles.

15. The fluorometer according to claim 3, wherein the fluorometer is suitable for being mounted on any type of underwater system, whether autonomous or wired, such as gliders, profiling floats, stationary or drifting buoys, propeller vehicles and remotely operated vehicles.

16. The fluorometer according to claim 4, wherein the fluorometer is suitable for being mounted on any type of underwater system, whether autonomous or wired, such as gliders, profiling floats, stationary or drifting buoys, propeller vehicles and remotely operated vehicles.

17. The fluorometer according to claim 5, wherein the fluorometer is suitable for being mounted on any type of underwater system, whether autonomous or wired, such as gliders, profiling floats, stationary or drifting buoys, propeller vehicles and remotely operated vehicles.

18. The fluorometer according to claim 6, wherein the fluorometer is suitable for being mounted on any type of underwater system, whether autonomous or wired, such as gliders, profiling floats, stationary or drifting buoys, propeller vehicles and remotely operated vehicles.

19. A submersible fluorometer intended to be mounted on an underwater system for studying fluorescent aromatic compounds of the aquatic environment, each aromatic compound having at least one fluorophore, of the type comprising:

an excitation module suitable for exciting the fluorophore; and a detection module suitable for detecting the light emitted by the excited fluorophore, wherein the excitation module comprises a first light source having a first UV LED and having a first wavelength smaller than 300 nm, and the excitation module includes a second light source having a second UV LED and having a second wavelength smaller than 300 nm, the first and second wavelengths being different from each other, and the fluorometer includes an electrical circuit including a plurality of printed circuits positioned below one another, wherein the electrical circuit includes a monitoring circuit, and wherein the plurality of printed circuits include three printed circuits that are substantially parallel to each other, concentric to a central axis (A-A) of the fluorometer, and are positioned below one another in vertical registration with each other.

* * * * *